US00PP11242P

United States Patent [19]

Kordes

[11] Patent Number: Plant 11,242

[45] Date of Patent: Feb. 22, 2000

[54] MINIATURE ROSE PLANT NAMED 'KORSTOFFEIN'

[75] Inventor: Wilhelm Kordes, Sparrieshoop, Germany

[73] Assignee: Bear Creek Garden, Inc., Medford, Oreg.

[21] Appl. No.: 09/046,310

[22] Filed: Mar. 23, 1998

[51] Int. Cl.[7] ..... A01H 5/00

[52] U.S. Cl. ..... Plt./116

[58] Field of Search ..... Plt./116, 118, 119, Plt./123, 125, 126

*Primary Examiner*—Howard J. Locker

*Attorney, Agent, or Firm*—Klarquist Sparkman Campbell Leigh & Whinston LLP

[57] ABSTRACT

A miniature rose plant, a spontaneous mutant of 'KORkleiva', having novel flower color, the petals being a yellow-orange on their upper surface and pink on their lower surface with a yellow-orange rib.

1 Drawing Sheet

The present invention relates to a new and distinct variety of rose plant of the miniature class which was originated by me by discovering in a greenhouse of W. Kordes Rosenschulen G.M.B.H. & Co. KG in Sparrieshoop, Germany in November 1996, a novel flower color mutation upon a single branch of the variety 'KORkleiva' U.S. Plant Patent Application Ser. No. 09/046,313.

The variety 'KORstoffein' distinguishes from its parent 'KORkleiva' in that the outer exposed upper sides of the petals of 'KORkleiva' are Yellow-White Group 158B. Those of 'KORstoffein' are Yellow-Orange Group 19D. The reverse sides of the petals of 'KORkleiva' are Orange-White Group 159C. Those of 'KORstoffein' are Red Group 52D.

Asexual reproduction of this new variety by cuttings propagation, as performed at Sparrieshoop, Germany and Somis and Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Parent.*—Spontaneous mutant of 'KORkleiva' U.S. Plant Application Ser. No. 09/046,313.

Classification:

*Botanical.*—Rosa hybrida.

*Commercial.*—Miniature.

FLOWER

Observations made from specimens grown in a greenhouse environment at Sparrieshoop, Germany and at Somis, Calif. from January, 1997 to January, 1998.

Blooming habit: Continuous.

Bud:

*Size.*—Three-quarter inches long when the petals start to unfurl.

*Form.*—The bud form is long, pointed ovoid.

*Color.*—When sepals first divide, bud color is Red Group 52D with the veins, especially the mid-rib, being Orange-White Group 159D. When half blown, the upper sides of the petals are Yellow-Orange Group 19D, except for the innermost petals which are Yellow-Orange Group 21C; and the lower sides of the petals are Red Group 52D with the veins, especially the mid-rib, being Yellow-Orange Group 19D.

*Sepals.*—Color: Green group 138B. Surface texture: Covered in fine hairs. There are three lightly appendaged sepals. There are two unappendaged sepals with hairy edges.

*Receptacle.*—Color: Green Group 146C. Shape: Funnel. Size: Small (⅜"×⅜"). Surface: Smooth.

*Peduncle.*—Length: Short (1¼"). Surface: Glandular. Color: Green Group 137C. Strength: Stiff, erect.

Bloom:

*Size.*—Small. Average open size is 1½ to 1¾ inches.

*Borne.*—Singly.

*Stems.*—Short (5"), strong.

*Form.*—When first open: High centered. Permanence: Retains its form to the end; outer petal edges curl back.

*Petalage.*—Number of petals under normal conditions: 25–30.

*Color.*—The upper sides of the petals are Yellow-Orange Group 19D except for the innermost petals which are Yellow-Orange Group 21C. The reverse sides of the petals are Red Group 52D with the veins, especially the mid-rib, being Yellow-Orange Group 19D. The base of each petals has a small (3/16"×3/16"), Yellow Group 4A, half moon at the point of attachment. The major color on the upper sides is Yellow-Orange Group 19D.

*Variegations.*—Occasional greenish-white streaks on the guard petals.

*Discoloration.*—At the end of the first day: No change. At the end of the third day: No change. By day five or six as the flower opens, the interior petals unfold and change from Yellow-Orange Group 21C to Yellow-Orange Group 19D. This color remains stable to petal drop after day 25.

*Fragrance.*—None.

Petals:

*Texture.*—Thick, leathery.

*Shape.*—Round.

*Form.*—Tips slightly recurved.

*Arrangement.*—Imbricated. Petaloids in the center are few and small. A blossom will have from 3 to 11 petaloids, which range in size from 2–7 mm in length, and 3–5 mm in width. Both surfaces are Yellow-Orange 21C.

*Persistence.*—Drop off cleanly before drying.

*Lastingness.*—On the plant: Very long (twenty-five days). As a cut flower: Very long (twenty-five days).

Reproductive parts:

*Anthers.*—Size: Medium. Quantity: Many. Color: Yellow. Arrangement: Regular around styles.

*Filaments*—Color: Yellow.

*Pollen.*—Color: Gold yellow.

*Styles.*—Color: Reddish.

*Stigmas.*—Color: Greenish-white.

Plant:

*Form.*—Bush.

*Growth.*—Vigorous; upright; branching; compact.

*Mature plant.*—At maturity, height is twenty-four inches, width is eighteen inches as a garden rose. When grown as a pot rose in a 4"×3½" pot, the plant is seven inches in height and six inches wide.

*Foliage.*—Number of leaflets on normal mid-stem leaves: Five.

*Size.*—Small. (3"×2 ").

*Quantity.*—Abundant.

*Color.*—New foliage: Upper and lower surfaces: Greyed-Red Group 178C. Old foliage: Upper surface: Green Group 139A. Lower surface: Green Group 139C.

*Shape.*—Pointed oval.

*Texture.*—Upper side: Glossy, smooth.

*Edge.*—Serrated.

*Serration.*—Single, small.

*Petiole rachis.*—Color: Greyed-Purple Group 183C.

*Petiole underside.*—Smooth, with occasional prickles.

*Stipules.*—Short (5/16"); serrated, bearded.

*Disease resistance.*—Resistant to mildew under normal growing conditions at Sparrieshoop, Germany and Somis, Calif.

Wood:

*New wood.*—Color: Greyed-Purple Group 183A. Bark: Smooth.

*Old wood.*—Color: Green Group 137B. Bark: Smooth.

Prickles:

*Quantity.*—On main canes from base: Few. On laterals from main canes: Few.

*Form.*—Short; straight to hooked slightly downward.

*Color when young.*—Greyed-Purple Group 183B.

*Color when mature.*—Greyed-Orange Group 177D.

Small Prickles:

*Quanity.*—On main stalks: None. On laterals: None.

I claim:

1. A new and distinct variety of rose plant of the miniature class, a mutation of the variety 'KORkleiva', substantially as herein shown and described, characterized particularly as to novelty from its parent by its novel flower color, the petals being a yellow-orange on their upper surface and pink on their lower surface with a yellow-orange rib.

* * * * *

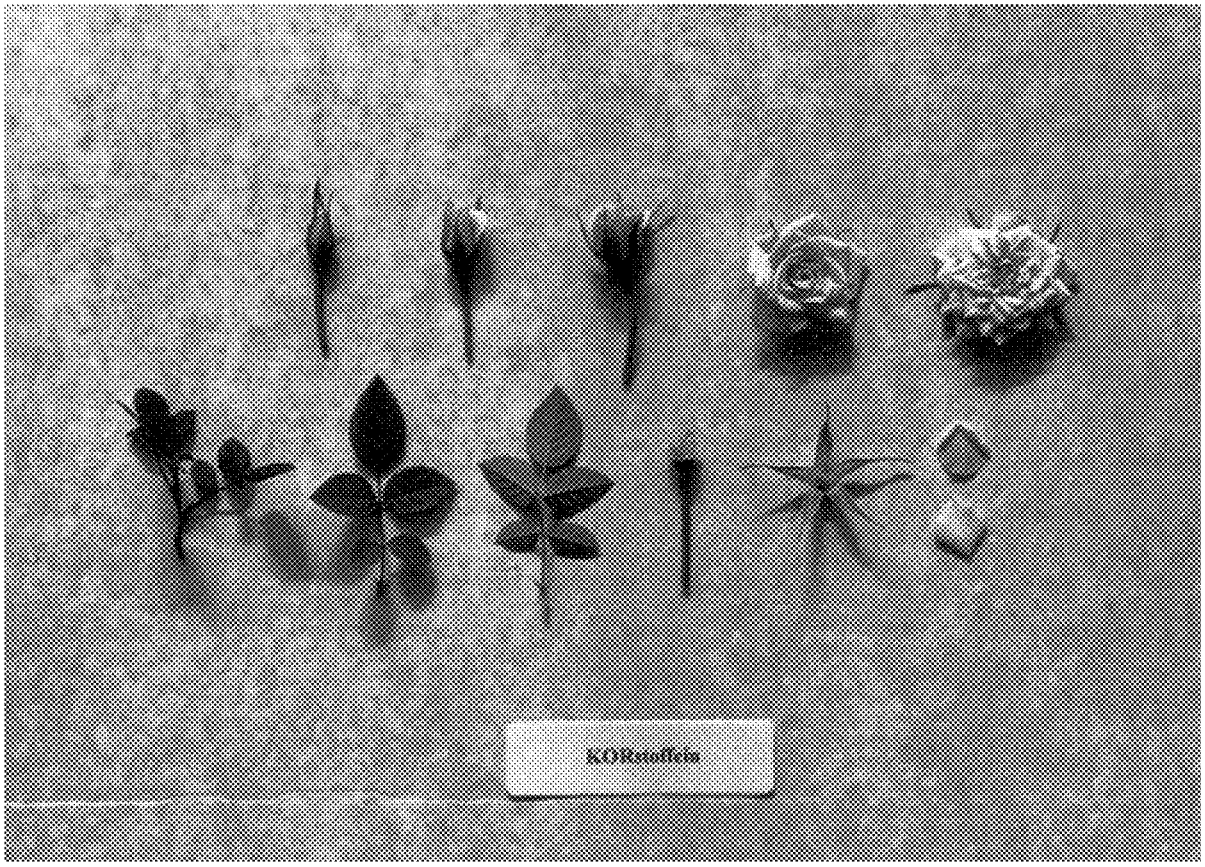
KORuffle